United States Patent [19]

Whiting

[11] Patent Number: Plant 6,345

[45] Date of Patent: Oct. 18, 1988

[54] ZOYSIA GRASS PLANT

[76] Inventor: Hubert F. Whiting, 14317 Woods Valley Rd., Valley Center, Calif. 92082

[21] Appl. No.: 926,963

[22] Filed: Oct. 31, 1986

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

I disclose that my herein invention of a new variety of Zoysia grass plant was discovered by me through my cross-pollinating of selected varieties of Zoysia grass plants, then through asexual repropagation I selected the new and distinct variety of Zoysia grass plant ZT-26. This new variety of Zoysia grass plant produces an excellent turfgrass from stolons and rhizomes with a considerably faster establishment growth rate and with a more open texture that develops less thatch and retains superior green color during the winter period when compared to the closest known varieties of the species.

2 Drawing Sheets

1

The present invention and discovery relates to a new and distinct variety of Zoysia grass plant, which was developed by me through s series of cross-pollination of collected varieties of Zosyia grass plants. This cross-pollination was done by me at Fallbrook, Calif., about 34 degrees north latitude. I harvested seeds from this cross-pollination of selected varieties of Zoysia grass plants and planted these seeds out in germinating trays. About six weeks after the seeds germinated, I selected the one hundred most rapidly establishing plants. I then transplanted each separate seedling into one gallon containers. As these seedlings grew and developed, I once again selected the most aggressively establishing and most desirable for turfgrass potential; this left forty five seedlings. These forty five seedlings were then each individually broken up by me into small pieces of stolons. I then planted these small pieces of stolons into the soil in an area that was three feet square. When this process was completed, I had forty five individual seedlings planted in forty five three foot square plots, all asexually transplanted by me. The location of this transplanting was at Fallbrook, Calif. Once these forty five three foot square plots became established through the spreading of the planted stolons, I formed a turfgrass surface through regular mowing. I again made selections from the forty five plots. The selections I made this time were again individually transplanted by me asexually, by breaking sufficient stolon material of each separate selection to further replant the now ten selections into larger individual separate plots of ten feet by eight feet. Once these larger plots became established through the spreading of the planted stolons. I formed a turfgrass surface through regular mowing. I again made selections from these ten plots. The new claimed variety of Zoysia grass plant, is one of those selections, and which I have designated ZT-26. This new selected variety of Zoysia grass plant spread by stolons and rhizomes to produce an excellent turfgrass surface when regularly mown. I observed that this new claimed variety of Zoysia grass plant, produced a 40% greater stolon growth rate at optimum temperatures and a 70% greater stolon growth rate at low winter temperatures, when compared to the closest known variety of Zoysia grass plant known as El Toro. This new claimed variety of Zoysia grass plant ZT-26 also produces a more open textured growth characteristic which produces less

2 thatch, and during the winter period retained better green color than the closest known variety of Zoysia grass plant. During the continued asexual reproduction by stolons, I have confirmed that the above-described characteristics are transmitted through succeeding propagations, and have confirmed that the new claimed variety of Zoysia grass plant has the following unique combination of characteristics. The new and distinct variety of Zoysia grass plant is illustrated in the accompanying color photographs, with the photographs of the closest known Zoysia grass plant known as El Toro. The most noticeable variations between the new claimed variety of Zoysia grass plant and the closest known variety of Zoysia grass plant known as El Torro, is that the new claimed variety is dark yellowish green color with a more open texture and a rapid stolon establishment growth rate; the new claimed variety of Zoysia grass plant has stigmas of pale yellow green with newly formed anthers before dehiscene of pale greenish yellow and stolon nodes further apart; the new claimed variety of Zoysia grass plant is glabrous, except for two or three hairs at the top of the sheath at the sides of the ligule, which is a very small ciliate fringe.

In the drawings:

FIG. 1 is a photograph of three spikes taken from the same test area, with two spikes of the new claimed variety at the side of the closest known variety of Zoysia grass plant known as El Toro; this photograph shows the pale yellow green colored stigmas with pale greenish yellow colored anthers and glumes of light yellow green as defined by the ISCC-NBS centroid color chart of the new claimed Zoysia grass plant, compared to the closest known variety of Zoysia grass plant which has yellowish white stigmas with dark purplish red anthers and glumes of very dark purplish red as defined by ISCC-NBS centroid color chart.

FIG. 2 is a photograph of two stolons taken from the same test area. This photograph shows the stolon of the new claimed variety of Zoysia grass plant on the right of the photograph with nodes wider apart and light yellow green color as defined by the ISCC-NBS centroid color chart, when compared to the closest known variety of Zoysia grass plant known as El Toro, which is on the left of the photograph and that has nodes closer together with stolon color of very dark purplish red as defined by the ISCC-NBS centroid color chart.

FIG. 4 is a photograph of a culm of the closest known variety of Zoysia grass plant known as El Toro taken from the same test area. This photograph shows a ring of long hairs protruding from the ligule and the long hairs at the top of the sheath.

Figure 1:
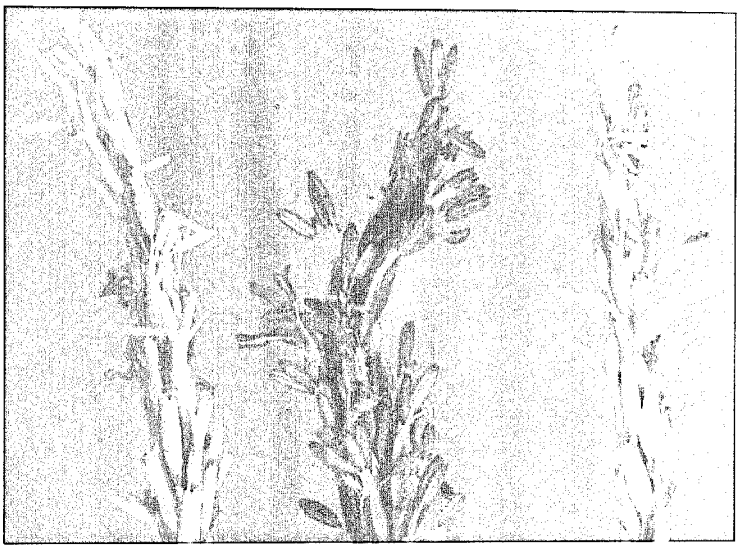
Figure 2:
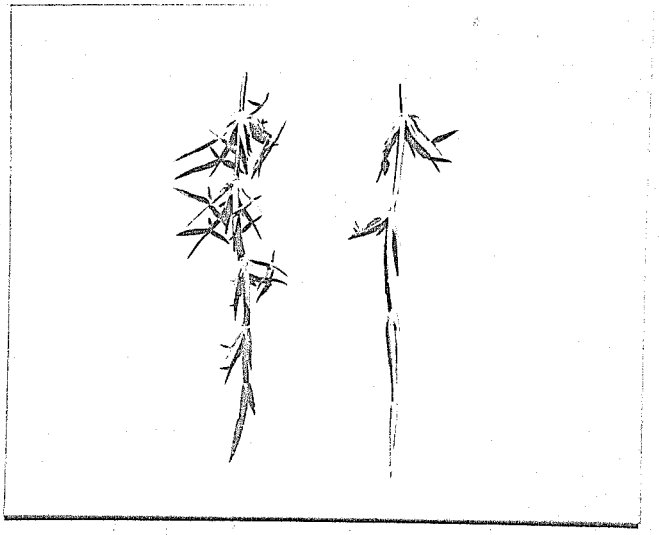
Figure 3:
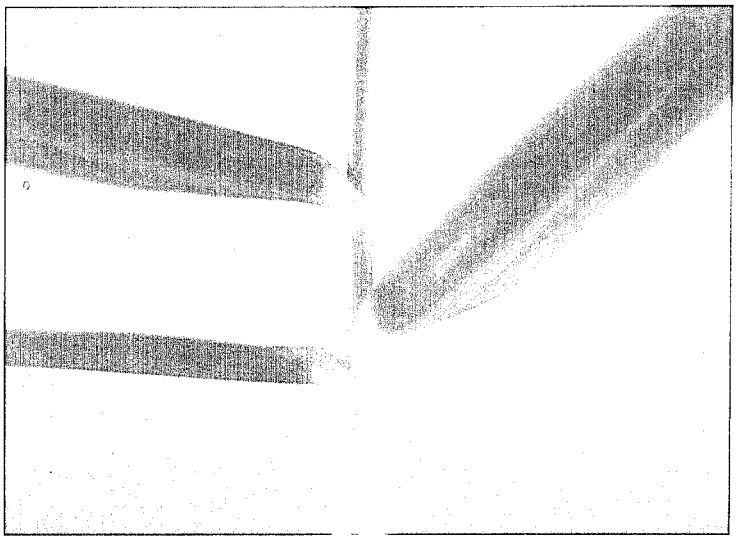
FIG. 3 is a photograph of a culm of the new claimed variety of Zoysia grass plant taken from the same test area. This photograph shows the glabrous sheath and leaves.

FIG. 5 is a photograph of two leaves taken from the same test area; this photograph shows the leaf of the new claimed variety of Zoysia grass plant on the right of the photograph with the sheath bent underneath to show the glabrous area of the ligule when compared to the leaf of the closest known variety of Zoysia grass plant known as El Toro which is on the left and shows a ring of long hairs at the ligule area.

The following photographs show the electrophoresis isoenzyme banding patterns, using the phosphoglucomutase (PGM), Easterase (EST), and Lucine Aminopeptidase (LAP) isoenzymes. Electrophoresis and isoenzyme techniques have been documented for grass plant identification, (Wu, Harivandi, Harding, and Davis).

FIG. 6 This photograph shows the electrophoresis zymogram patterns of the esterase (EST) isoenzyme banding pattern of the new claimed variety of Zoysia grass plant ZT-26, with the closest known variety of Zoysia grass plant as El Toro, taken from the same test area.

FIG. 7 This photograph shows the electrophoresis zymogram patterns of the phosphoglucomutase (PGM) isoenzyme banding pattern of the new claimed variety of Zoysia grass plant ZT-26, with the closest known variety of Zoysia grass plant known as El Toro, taken from the same test area.

FIG. 8 This photograph shows the electrophoresis zymogram patterns of the lucine aminopeptidase (LAP) isoenzyme banding pattern of the new claimed variety of Zoysia grass plant ZT-26, with the closest known variety of Zoysia grass plant known as El Toro, taken from the same test area.

A detailed description of the new and distinct variety of Zoysia grass plant ZT-26 is:

(a) An attractive dark yellowish green color, color number 137.d.yG, of the ISCC-NBS centroid color chart.

(b) The grass is low-growing, erect in habit.

(c) The grass spreads by stolons and rhizomes, forming a dense, uniform surface, with an extensive root system. The stolons are light yellow green, color number 119L. YG, of the ISCC-NBS centroid color chart, with the stolon nodes 3.5–4 centimeters apart.

(d) Culms vary in height from 14–16 centimeters.

(e) Leaves rolled in bud shoot.

(f) The leaf blade is flat, and gradually tapering to an acute point.

(g) The first mature leaf is 3–4 millimeters in width and 5–9 centimeters in length.

(h) The leaf blade is glabrous.

(i) The ligule is a very small ciliate fringe.

(j) Auricles are absent.

(k) The collar is broad, and continuous.

(l) The sheath is glabrous, except for two or three hairs at the top of the sheath at the sides of the ligule; the sheath is split with separate margins.

(m) The entire plant is glabrous, except at the top of the sheath where two or three hairs are present at the sides of the ligule.

(n) The inflorescence consists of a single spike at the top of the main stem.

(o) The spike contains stigmas of pale yellow green color, color number 121. p.YG of the ISCC-NBS centroid color chart, and anthers of pale greenish yellow color, color number 104.p.gY of the ISCC-NBS centroid color chart; the glumes are 2–3 millimeters long, blunt at their base, pointed at their tips and light yellow green color, color number 119.L.YG of the ISCC-NBS centroid color chart.

A detailed description of the closest known variety of the species of Zoysia grass plant is known and identified as El Toro.

(a) The grass is a dark green color, color number 146.d.G, of the ISCC-NBS centroid color chart.

(b) The grass is low-growing, erect in habit.

(c) The grass spreads by stolons and rhizomes, forming a dense uniform surface with an extensive root system. The stolons are very dark purplish red color, color number 260.v.d.pR of the ISCC-NBS centroid color chart, with the stolon nodes 2.5–3 centimeters apart.

(d) Culms vary in height from 13–15 centimeters.

(e) Leaves rolled in bud shoot.

(f) The leaf blade is flat, and gradually tapering to an acute point.

(g) The first mature leaf is 4–5 millimeters in width and 4–7 centimeters in length.

(h) The leaf blade is pubescent on the upper leaf surface.

(i) The ligule is a small ciliate fringe with a ring of dense long hairs 3–4 millimeters long.

(j) Auricles are absent.

(k) The collar is broad and continuous.

(l) The sheath is glabrous, except at the top of the sheath, where it is densely pubescent with hairs 3–4 millimeters long; the sheath is split with separate margins.

(m) The entire plant is glabrous, except at the top of the sheath where dense long hairs at the sides of the ligule are present, with the upper leaf blade surface pubescent.

(n) The inflorescence consist of a single spike at the top of the main stem.

(o) The spike contains stigmas of yellowish white color, color number, 92.y White of the ISCC-NBS centroid color chart, and anthers of dark purplish red color, color number 259.d.pR of the ISCC-NBS centroid color chart; the glumes are 2–3 millimeters long, blunt at their base, pointed at their tips, and are very dark purplish red color, color number, 260.v.d.pR of the ISCC-NBS centroid color chart.

Having now described the new and distinct variety of Zoysia grass plant ZT-26 which I have discovered and asexually reproduced, I claim:

1. A new and distinct variety of Zoysia grass plant, ZT-26, herein shown and described by a dark yellowish green, as defined by the centroid color chart; this new claimed variety produces a faster establishment growth rate, and a superior green color retention during the winter period, with a more open growth characteristic that produces less thatch build-up; the anthers of the new claimed variety of Zoysia grass plant are pale greenish yellow, as defined by the ISCC-NBS centroid color chart; the stigmas are pale yellow green color, as defined by the ISCC-NBS centroid color chart; the stolons of the new claimed variety of Zoysia grass plant, are wider apart with a light yellow green color, as defined by the ISCC-NBS centroid color chart; the entire plant of the new claimed variety of Zoysia grass plant is glabrous, except for two or three hairs at the top of the sheath at the sides of the ligule, with the ligule a small ciliate fringe; the new claimed variety of Zoysia grass plant, ZT-26, when using the electrophoresis banding pattern method, shows a distinct uniqueness, when compared to the closest known variety of Zoysia grass plant.

* * * * *

FIG.4.
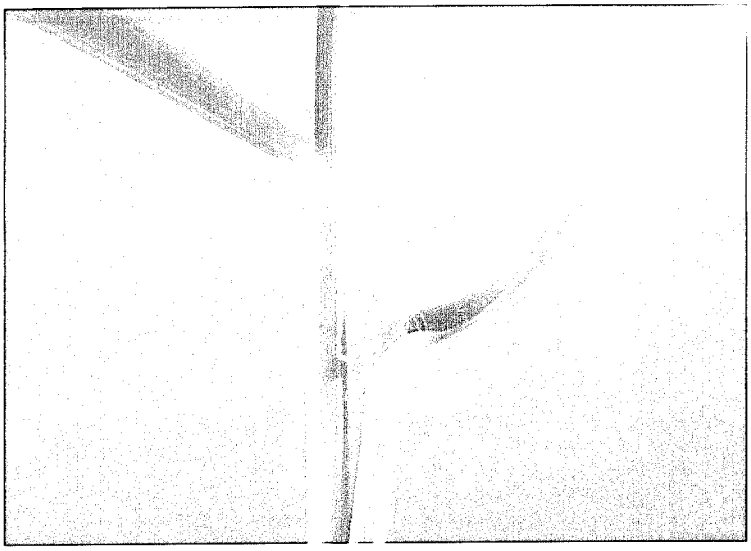
FIG.5.
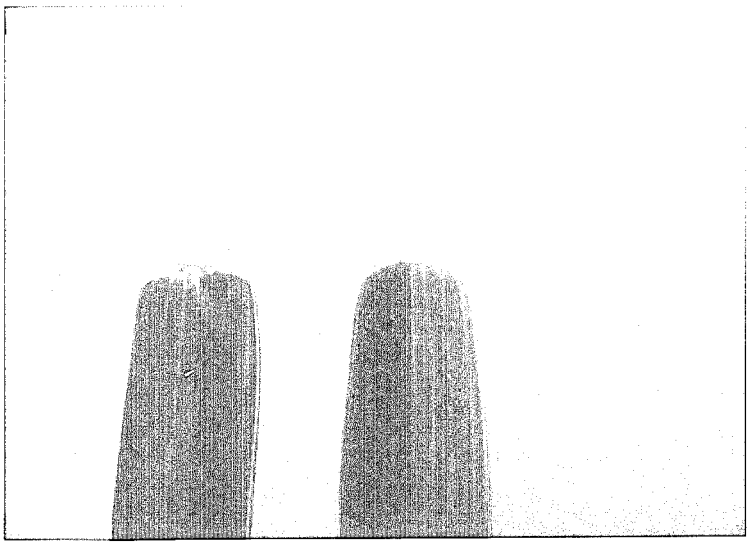
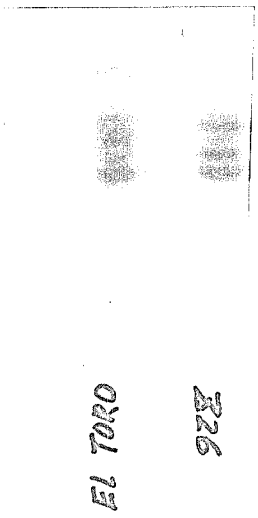
FIG.6
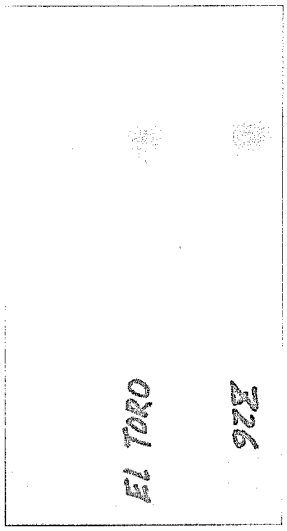
FIG.7
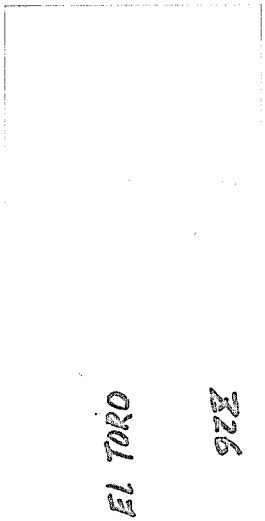
FIG.8